United States Patent [19]

Shigehara et al.

[11] Patent Number: 5,763,439
[45] Date of Patent: Jun. 9, 1998

[54] PYRIDAZINONE DERIVATIVES OR THEIR SALTS, PROCESSES FOR THEIR PRODUCTION, AND ANTI-SHOCK AGENTS CONTAINING THEM

[75] Inventors: Itaru Shigehara; Shinji Odawara; Hiroshi Okada; Hirohiko Kimura; Masato Omatsu; Hitoshi Nakayama; Rie Higuchi; Taki Takenami, all of Kusatsu, Japan

[73] Assignee: Ishihara Sangyo Kaisha Ltd., Osaka, Japan

[21] Appl. No.: 602,799

[22] PCT Filed: Aug. 22, 1994

[86] PCT No.: PCT/JP94/01380

§ 371 Date: Mar. 4, 1996

§ 102(e) Date: Mar. 4, 1996

[87] PCT Pub. No.: WO95/07264

PCT Pub. Date: Mar. 16, 1995

[30] Foreign Application Priority Data

Sep. 6, 1993 [JP] Japan ............... 5-246344
Apr. 1, 1994 [JP] Japan ............... 6-087999

[51] Int. Cl.$^6$ .............. A61K 31/50; C07D 401/12; C07D 237/22; C07D 417/12
[52] U.S. Cl. .............. 514/247; 514/252; 544/238; 544/239; 544/240; 544/241
[58] Field of Search .............. 544/238, 239, 544/240, 241; 514/247, 252

[56] References Cited

U.S. PATENT DOCUMENTS 5,079,261  1/1992  Serhan et al. .............. 514/552
5,098,900  3/1992  Mutsukado et al. .......... 544/238

FOREIGN PATENT DOCUMENTS

76511/91  11/1991  Australia.
186817   7/1986   European Pat. Off..
275997   7/1988   European Pat. Off..
376079   7/1990   European Pat. Off..
482208   4/1992   European Pat. Off..

OTHER PUBLICATIONS

Derwent Abstract for WO9013292 (Nov. 15, 1990), Serhan et al.

Takaya et al, *Chemical Abstracts* vol. 90, No. 152105 (1979).

*Primary Examiner*—Emily Bernhardt
*Attorney, Agent, or Firm*—Oblon, Spivak, McClelland, Maier & Neustadt, P.C.

[57] ABSTRACT

A pyridazinone derivative of the formula (I) or a pharmaceutically acceptable salt thereof:

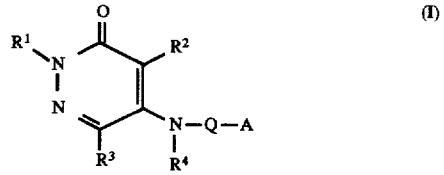

wherein Q, A, and $R^1$–$R^4$ are as defined herein, useful as an anti-shock agent.

12 Claims, No Drawings

PYRIDAZINONE DERIVATIVES OR THEIR SALTS, PROCESSES FOR THEIR PRODUCTION, AND ANTI-SHOCK AGENTS CONTAINING THEM

TECHNICAL FIELD

The present invention relates to novel pyridazinone derivatives or salts thereof, processes for their production and pharmaceutical compositions containing them as active ingredients. More particularly, it relates to anti-shock agents.

BACKGROUND ART

Japanese Unexamined Patent Publication No. 267560/1986 discloses that a 3-pyridazinone compound having $C_{2-5}$ alkyl at the 2-position, H, $C_{1-3}$ alkyl, Cl or Br at the 4-position and substituted phenylmethylamino at the 5-position is useful as an antiallergic agent.

WO91/16314 discloses that a pyridazinone derivative having Ce, Br, H or CN at the 4-position, $-N(R^3)CH(R^4)Ar$ at the 5-position, and $OR^2$ wherein $R^2$ is $A^1-Y^1$ (wherein $A^1$ is alkylene, and $Y^1$ is $CO_2R^5$, CN, $OR^6$, thienyl, pyridyl, etc.) or $A^2-y^2$ (wherein $A^2$ is alkylene, and $y^2$ is phenyl), at the 6-position, is useful as a preventive or therapeutic agent for e.g. thrombotic diseases, congestive failure, hypertension, asthma or immediate allergy.

Japanese Unexamined Patent Publication No. 201994/1993 discloses that a pyridazinone derivative having a diphenylmethyl group at the 2-position is useful as a therapeutic agent for hypertension, congestive failure or chronic renal diseases.

J. Heterocycl. Chem. (1990) 27 (3) 471–477 discloses 5-benzylamino-6-methoxycarbonyl-2-phenylpyridazin-3(2H)-one at page 475, left column, lines 19–20.

Yakugaku Zasshi (Pharmacological Journal) (1978) 98 (10) 1421–1427 discloses at page 1425, lines 3–7, 5-[N-benzyl-N-(2-trityloxyethyl)amino]-4-ethoxy-2-methyl-3(2H)-pyridazinone (XIII) as an intermediate for the synthesis of urinary methabolites of 4-ethoxy-2-methyl-5-morpholino-3(2H)-pyridazinone having antiinflammatory effects.

However, the compounds of the present invention are different in the chemical structure from the compounds disclosed in the above-mentioned Japanese Unexamined Patent Publication No. 267560/1986, WO91/16314, Japanese Unexamined Patent Publication No. 201994/1993, J. Heterocycl. Chem. (1990) 27 (3) 471–477 and Yakugaku Zasshi (1978) 98 (10) 1421–1427.

In a broad sense, shock is regarded as an ischemic diseases, but it is caused by various diseases such as septic shock, hemorrhagic shock and cardiogenic shock. The septic shock occurs to a patient seriously diseased with a Gram negative bacteria infectious disease, and it is one of serious diseases, whereby the patient is likely to be killed when the symptom is really bad. There are many patients particularly in the field of emergency medical care. As an anti-shock agent, steroids or Miraclid has been used which is one of protease inhibitors. However, even then, the death rate is still high, and development of a more effective drug is desired.

DISCLOSURE OF THE INVENTION

It is an object of the present invention to provide a novel pyridazinone derivative or a salt thereof which is useful as an anti-shock agent, a process for its production and a pharmaceutical composition containing it as an active ingredient.

The present inventors have prepared shock models of small animals such as rats and mice and have conducted extensive researches with an aim to improve the survival rate. As a result, they have found that pyridazinone derivatives having a certain specific chemical structure exhibit excellent anti-shock effects. The present invention has been accomplished on the basis of this discovery.

That is, the present invention provides a pyridazinone derivative of the formula (I) or a pharmaceutically acceptable salt thereof:

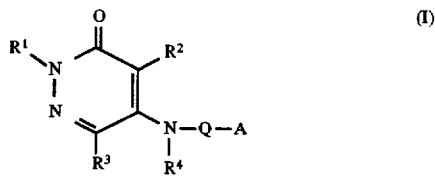

wherein Q is $-CH_2-$ or $-CO-$, A is a furanyl group which may be substituted, a thienyl group which may be substituted, a pyridyl group which may be substituted, a pyridyl N-oxide group which may be substituted, a thiazolyl group which may be substituted, or a phenyl group which may be substituted, $R^1$ is a hydrogen atom, an alkyl group which may be substituted, an alkenyl group which may be substituted, an alkynyl group which may be substituted, or a phenyl group which may be substituted, $R^2$ is a hydrogen atom, a cyano group, an alkyl group which may be substituted, a hydroxyl group, an alkoxy group, a dioxanyl group which may be substituted by an alkyl group, $-CH=N-R^5$, $-S(O)_nR^6$, $-N(R^7)R^8$, or $-COR^9$, $R^3$ is a hydrogen atom, a cyano group, a nitro group, an alkoxy group, a carboxyl group or an alkoxycarbonyl group, $R^4$ is a hydrogen atom, or an alkyl group which may be substituted, $R^5$ is an alkoxy group, or a pyridylmethyl group, $R^6$ is an alkyl group which may be substituted, or an alkenyl group, each of $R^7$ and $R^8$ independently is a hydrogen atom, an alkyl group, an alkylsulfonyl group, a phenylsulfonyl group which may be substituted, a formyl group, an alkylcarbonyl group which may be substituted by a halogen atom, a cycloalkylcarbonyl group, or a benzoyl group which may be substituted, $R^9$ is a hydrogen atom, an alkoxy group, a hydroxyl group, or an amino group which may be substituted, n is 0, 1 or 2, provided that when $R^2$ is a hydrogen atom, an alkyl group or an alkoxy group, and Q is $-CH_2-$, A is a furanyl group which may be substituted, a thienyl group which may be substituted, a pyridyl group which may be substituted, a pyridyl N-oxide group which may be substituted, or a thiazolyl group which may be substituted, processes for its production, and an anti-shock agent containing it as an active ingredient.

Now, the present invention will be described in detail with reference to the preferred embodiments.

In the formula (I), the substituent for each of the furanyl group which may be substituted, the thienyl group which may be substituted, the pyridyl group which may be substituted, the pyridyl N-oxide group which may be substituted and the thiazolyl group which may be substituted, as defined by A, the phenyl group which may be substituted, as defined by A or $R^1$, or the phenylsulfonyl group which may be substituted and the benzoyl group which may be substituted, as defined by $R^7$ or $R^8$, may, for example, be a halogen atom, a nitro group, a trifluoromethyl group, a $C_{1-3}$ alkyl group, a $C_{1-3}$ alkoxy group, an amino group or a mono- or di-$C_{1-3}$ alkylamino group. The number of substituents may be one or more. In the case of two or more substituents, they may be the same or different.

The substituent for each of the alkyl group which may be substituted, the alkenyl group which may be substituted and the alkynyl group which may be substituted, as defined by $R^1$, or the alkyl group which may be substituted, as defined by $R^2$ or $R^4$, may, for example, be a halogen atom, a hydroxyl group, a $C_{1-3}$ alkoxy group, a $C_{1-3}$ alkylthio group, a $C_{1-3}$ alkylcarbonyloxy group, a $C_{1-3}$ alkoxycarbonyloxy group, a phenyl group, an amino group, a mono- or di-$C_{1-3}$ alkylamino group, a $C_{1-3}$ alkylsulfonylamino group, a cyano group, a carboxyl group, or a $C_{1-3}$ alkoxycarbonyl group. The number of substituents may be one or more. In the case of two or more substituents, they may be the same or different.

The dioxanyl group which may be substituted by an alkyl group, as defined by $R^2$, means a 1,3-dioxan-2-yl group which may be substituted by a $C_{1-3}$ alkyl group.

The substituent for the alkyl group which may be substituted, as defined by $R^6$, may, for example, be a $C_{1-3}$ alkoxycarbonyl group.

The substituent for the amino group which may be substituted as defined by $R^9$, may, for example, be a $C_{1-3}$ alkyl group, or a $C_{1-3}$ alkylcarbonyl group.

In this specification, the halogen atom means F, Cl, Br, or I.

The alkyl group which may be substituted, as defined by $R^1$, the alkyl group which may be substituted and the alkyl moiety of the alkoxy group, as defined by $R^2$, the alkyl moiety of the alkoxy group and the alkoxycarbonyl group, as defined by $R^3$, the alkyl group which may be substituted, as defined by $R^4$, the alkyl moiety of the alkoxy group as defined by $R^5$, the alkyl group which may be substituted, as defined by $R^6$, the alkyl group, or the alkyl moiety of the alkylsulfonyl group, or the alkylcarbonyl group which may be substituted by a halogen atom, as defined by $R^7$ or $R^8$, or the alkyl moiety of the alkoxy group as defined by $R^9$, may be a $C_{1-8}$ linear or branched alkyl group. For example, methyl, ethyl, propyl, isopropyl, butyl, sec-butyl, tert-butyl and pentyl may be mentioned.

The alkenyl group which may be substituted, as defined by $R^1$, or the alkenyl group as defined by $R^6$ may be a $C_{2-8}$ linear or branched alkenyl group. For example, ethenyl, 1-propenyl, 2-propenyl, butenyl and pentenyl may be mentioned.

The alkynyl group which may be substituted, as defined by $R^1$, may be a $C_{2-8}$ linear or branched alkynyl group. For example, ethynyl, 1-propynyl, 2-propynyl, butynyl and pentynyl may be mentioned.

The cycloalkylcarbonyl group as defined by $R^7$ or $R^8$ may be the one having a $C_{3-8}$ cycloalkyl moiety.

The compound of the formula (I) may form a salt, such a salt may be any salt so long as it is pharmaceutically acceptable. For example, an alkali metal salt such as a sodium or potassium salt, an alkaline earth metal salt such as a calcium salt, an organic amine salt such as a triethanol amine salt or a tris(hydroxymethyl)aminomethane salt, an inorganic acid salt such as a hydrochloride, a sulfate or a nitrate, or an organic acid salt such as an acetate, a methane sulfonate, a lactate or a citrate, may be mentioned.

The following compounds are preferred as the pyridazinone derivatives or pharmaceutically acceptable salts thereof of the present invention.

(1) A compound of the formula (I), wherein Q is —$CH_2$—, or a pharmaceutically acceptable salt thereof.

(2) A compound of the formula (I), wherein A is a pyridyl group which may be substituted, or a pharmaceutically acceptable salt thereof.

(3) A compound of the formula (I), wherein $R^1$ is an alkyl group, or a pharmaceutically acceptable salt thereof.

(4) A compound of the formula (I), wherein $R^3$ is a hydrogen atom, or a pharmaceutically acceptable salt thereof.

A compound of the formula (I), wherein Q is —$CH_2$—, and A is a pyridyl group which may be substituted, or a pharmaceutically acceptable salt thereof, is more preferred.

Further, a compound of the formula (I), wherein $R^1$ is an alkyl group, $R^2$ is an alkyl group which may be substituted by a group selected from the group consisting of halogen, hydroxyl, $C_{1-3}$ alkoxy, $C_{1-3}$ alkylthio, $C_{1-3}$ alkylcarbonyloxy, $C_{1-3}$ alkoxycarbonyloxy, phenyl, amino, mono- or di-$C_{1-3}$ alkylamino, $C_{1-3}$ alkylsulfonylamino, cyano, carboxyl and $C_{1-3}$ alkoxycarbonyl, a cyano group or —$N(R^7)R^8$, and each of $R^7$ and $R^8$ independently is a hydrogen atom, an alkyl group, an alkylsulfonyl group, a phenylsulfonyl group which may be substituted, a formyl group, an alkylcarbonyl group which may be substituted by a halogen atom, a cycloalkylcarbonyl group, or a benzoyl group which may be substituted, or a salt thereof, is most preferred.

The most preferred compound or a salt thereof may, for example, be 4-hydroxymethyl-2-methyl-5-(4-pyridylmethylamino)pyridazin-3-(2H)-one, 2-tert-butyl-4-hydroxymethyl-5-(4-pyridylmethylamino)pyridazin-3-(2H)-one, 4-methoxymethyl-2-methyl-5-(N-methyl-3-pyridylmethylamino)pyridazin-3-(2H)-one, 4-methoxymethyl-2-methyl-5-(N-methyl-4-pyridylmethylamino)pyridazin-3-(2H)-one or 4-methoxymethyl-2-methyl-5-(4-pyridylmethylamino)pyridazin-3-(2H)-one, or salts thereof.

The compound of the formula (I) can be prepared, for example, by the following process (A), (B) or (C):

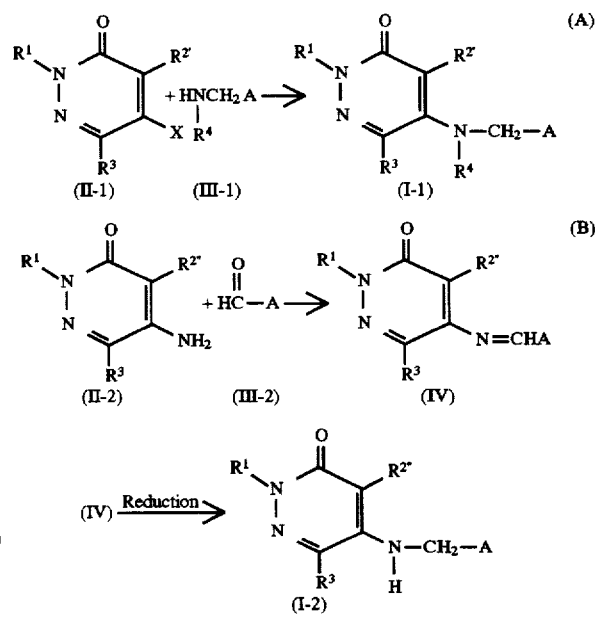

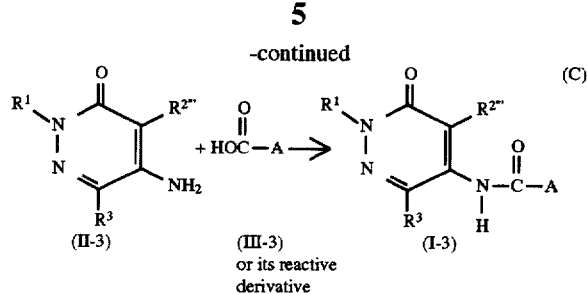

wherein A, $R^1$, $R^3$ and $R^4$ are as defined above, $R^{2'}$ is a hydrogen atom, a cyano group, an alkyl group which may be substituted, a dioxanyl group which may be substituted by an alkyl group, —CH=N—$R^5$, or —$COR^9$, X is a halogen atom, or a cyano group, $R^{2''}$ is a hydrogen atom, a hydroxyl group, an alkoxy group, —$S(O)_nR^6$, or —$N(R^7)R^8$, and $R^{2'''}$ is a hydrogen atom, a cyano group, an alkyl group which may be substituted, a hydroxyl group, an alkoxy group, —$S(O)_nR^6$, or —$N(R^7)R^8$.

Process (A)

A compound of the formula (I-1) can be prepared by reacting a compound of the formula (II-1) with a compound of the formula (III-1).

The solvent to be used for this reaction may, for example, be an alcohol such as methanol or ethanol, an ether such as dioxane or tetrahydrofuran, a ketone such as acetone or methyl ethyl ketone, a nitrile such as acetonitrile or propionitrile, an aprotic polar solvent such as dimethylformamide, N-methylpyrrolidone, dimethylsulfoxide or sulfolane, or pyridine. The reaction is carried out in a conventional water-soluble organic solvent. However, any other water-soluble organic solvent may be used for the reaction, so long as it presents no adverse effects to the reaction. Further, in some cases, the reaction can be carried out in a solvent mixture with water or in the absence of a solvent.

In this reaction, from 2 to 100 mols of the compound of the formula (III-1) may be used per mol of the compound of the formula (II-1), and as an additional base, an inorganic base or an organic base may be used. The inorganic base may, for example, be an alkali metal hydroxide such as sodium hydroxide or potassium hydroxide, a carbonate of an alkali metal or an alkaline earth metal such as potassium carbonate or calcium carbonate, an alkali metal hydride such as sodium hydride, or an alkali metal such as metal sodium. The organic base may, for example, be pyridine or triethylamine.

The reaction temperature is usually from –20° C. to +150° C., preferably from 0° C. to 80° C. The reaction time is usually from 0.5 to 48 hours, preferably from 0.5 to 18 hours.

Process (B)

A compound of the formula (I-2) can be obtained by reacting a compound of the formula (II-2) with a compound of the formula (III-2), followed by reduction by means of a reducing agent.

As the solvent for the reaction of the compound of the formula (II-2) with the compound of the formula (III-2), an alcohol such as ethanol or propanol, or an aromatic compound such as benzene or toluene, may be employed. This reaction can be conducted for from 1 to 18 hours, preferably from 2 to 8 hours, by means of e.g. a Dean Stark trap, and the reaction is conducted under heating and refluxing.

For the reduction, any reducing method may be employed so long as the imino group in the compound of the formula (IV) can be hydrogenated without decomposing the compound. For example, the reaction may be carried out by using as a reducing agent from 0.5 to 2 mols of sodium borohydride per mol of the compound of the formula (IV) and as a solvent, an alcohol such as methanol, ethanol or propanol at a reaction temperature of from 0° to 40° C., preferably from 10° to 30° C. for a reaction time of from 0.1 to 10 hours, preferably from 0.5 to 3 hours, to obtain the desired product.

Process (C)

A compound of the formula (I-3) can be obtained by reacting a compound of the formula (II-3) with a compound of the formula (III-3) or its reactive derivative. As the reactive derivative of the compound of the formula (III-3), an acid halide, an ester or an acid anhydride may be mentioned.

In the case of the compound of the formula (III-3), the desired product can be obtained by a single step by using as a solvent, a halogenated hydrocarbon such as methylene chloride or ethylene dichloride and a condensation agent such as dicyclohexylcarbodiimide or 1-ethyl-3-(3-dimethylaminopropyl)carbodiimide hydrochloride. The reaction temperature is from –10° C. to +40° C., preferably from 10° to 25° C., and the reaction time is from 0.5 to 48 hours, preferably from 1 to 18 hours. In the case of a reactive derivative of the compound of the formula (III-3), as a solvent, an alcohol such as methanol or ethanol, an ether such as dioxane or tetrahydrofuran, a ketone such as acetone or methyl ethyl ketone, a nitrile such as acetonitrile or propionitrile, or an aprotic polar solvent such as dimethylformamide, N-methylpyrrolidone, dimethylsulfoxide or sulfolane, may, for example, be employed. As the base, an inorganic base or an organic base may be employed. The inorganic base may, for example, be an alkali metal hydroxide such as sodium hydroxide or potassium hydroxide, a carbonate of an alkali metal or an alkaline earth metal such as anhydrous potassium carbonate or anhydrous calcium carbonate, an alkali metal hydride such as sodium hydride, or an alkali metal such as metal sodium. The organic base may, for example, be pyridine or triethylamine. The reaction temperature is from 20° to 150° C., preferably from 30° to 80° C. The reaction time is from 0.5 to 72 hours, preferably from 1 to 18 hours.

In the process (A), when $R^4$ in the compound of the formula (III-1) is H, the reaction of the process (A) may be followed by the following reaction.

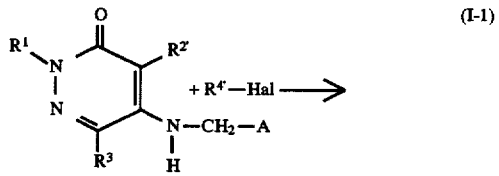

wherein $R^{4'}$ is an alkyl group which may be substituted.

This reaction can be carried out under the same reaction conditions as for the reaction of the above process (A).

Among compounds of the formula (II-1) of the present invention, the following compound of the formula (II-4) or a salt thereof is preferred as the intermediate.

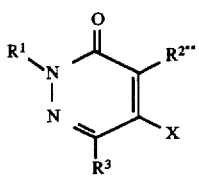

(II-4)

wherein X is a halogen atom, or a cyano group, $R^{2'''}$ is a cyano group, a substituted alkyl group, a dioxanyl group which may be substituted by an alkyl group, —CH=N—$R^5$, or —$COR^9$, and $R^1$, $R^3$, $R^5$ and $R^9$ are as defined above.

The compound of the formula (I) of the present invention is useful as an active ingredient of an anti-shock agent. This anti-shock agent is useful for prevention or therapy of bacterial endotoxin shock or a multiple organ failure thereby induced as well as ischemic diseases at heart, kidney, liver, gastrointestine, brain, etc.

To administer the compound of the present invention as the anti-shock agent, it is formulated alone or together with a pharmaceutically acceptable carrier into a drug composition suitable for peroral, parenteral, topical or per rectal administration, such as a tablet, a powder, a capsule, a granule, an injection drug, an ointment, an inhalant or a suppository, and it is administered in the form of such a drug formulation.

As a drug formulation suitable for peroral administration, a solid composition such as a tablet, a capsule, a powder, a granule or a troach; or a liquid composition such as a syrup suspension, may be mentioned. The solid composition such as a tablet, a capsule, a powder, a granule or a troach may contain a binder such as fine crystalline cellulose, gum arabic, tragacanth gum, gelatine or polyvinyl chloride; an excipient such as starch, lactose or carboxymethyl cellulose; a disintegrator such as arginic acid, corn starch or carboxymethyl cellulose; a lubricant such as magnesium stearate, light silicic anhydride or colloidal silicon dioxide; a sweetener such as sucrose; or a flavoring agent such as peppermint or methyl salicylate. The liquid composition such as a syrup or a suspension may contain sorbitol, gelatine, methyl cellulose, carboxymethyl cellulose, a vegetable oil such as a peanut oil, an emulsifier such as lecithin as well as a sweetener, a preservative, a colorant or a flavoring agent, as the case requires. Such a composition may be provided in the form of a dried formulation. These formulations preferably contain from 1 to 95% by weight of the active compound.

A drug formulation suitable for parenteral administration may, for example, be an injection drug. The injection drug may be prepared by dissolving the compound in the form of a salt in usual water for injection, or may be formulated into a formulation suitable for injection such as a suspension or an emulsion (in a mixture with a pharmaceutically acceptable oil or liquid). In such a case, it may contain benzyl alcohol as an antibacterial agent, ascorbic acid as an antioxidant, a pharmaceutically acceptable buffer solution or a reagent for adjusting the osmotic pressure. Such an injection drug preferably contains from 0.1 to 8% by weight of the active compound.

A drug formulation suitable for topical or per rectal administration may, for example, be an inhalant, an ointment or a suppository. The inhalant may be formulated by dissolving the compound of the present invention alone or together with a pharmaceutically acceptable inert carrier in an aerosol or nebulizer solution, or may be administered to the resiratory airway in the form of fine powder for inhalation. In the case of fine powder for inhalation, the particle size is usually not more than 50 μm, preferably not more than 10 μm. Such an inhalant may be used, if necessary, in combination with other antiasthematic agent or bronchodilator, such as Salbutamol, Ephedrine, Theophylline, Corticosteroid or ACTH (Adrenocorticotropic hormone).

An ointment may be prepared by a conventional method by an addition of a commonly employed base or the like. The ointment preferably contains from 0.1 to 30% by weight of the active compound.

The suppository may contain a carrier for formulation which is well known in this field, such as polyethylene glycol, lanolin, cacao butter or fatty acid triglyceride. The suppository preferably contains from 1 to 95% by weight of the active compound.

The above-mentioned drug compositions suitable for peroral, parenteral, topical or per rectal administration, may be formulated by conventional methods so that after administration to a patient, the active component will be rapidly discharged, gradually discharged or belatedly discharged.

The dose of the compound of the present invention as the anti-shock agent varies depending upon the type of the compound, the administration method, the condition of the patient or the animal to be treated. The optimum dose and the number of administration under a specific condition must be determined by the judgement of a competent doctor. Usually, however, a daily dose to an adult is from about 0.01 g to about 10 g, preferably from about 0.05 g to about 5 g. The dose of the compound of the present invention is preferably from about 0.01 mg to about 100 mg per administration.

Now, specific Formulation Examples of the anti-shock agent of the present invention will be given.

Formulation Example 1 (tablet)

(1) Compound No. 16 200 mg
(2) Lactose 150 mg
(3) Starch 30 mg
(4) Magnesium stearate 6 mg The above composition is tabletted so that the components (1) to (4) constitute one tablet.

Formulation Example 2 (powder or microgranule)

(1) Compound No. 21 200 mg
(2) Sugar ester (DK ester F-160, manufactured by Daiichi Kogyo) 180 mg
(3) Surfactant (Dekagreen 1-L, manufactured by Nikko Chemicals) 15 mg (4) Light silicic anhydride 25 mg The component (1) is wet-pulverized in an aqueous solution containing 5% of the component (3). Then, 180 mg of the component (2) is added thereto, and the mixture is freeze-dried. The dried product is pulverized and mixed with the component (4).

The mixture is formed into a powder or microgranule. Such a powder or microgranule may be sealed in a capsule to obtain a capsule drug.

Formulation Example 3 (hard gelatine capsule)

(1) Compound No. 33 250 mg
(2) Starch 200 mg
(3) Magnesium stearate 10 mg

The components (1) to (3) is packed in a hard gelatine capsule to obtain a hard gelatine capsule drug.

Formulation Example 4 (injection drug)

(1) Compound No. 57 1 g
(2) Glucose 10 g
(3) Distilled water for injection 200 ml The components (1) to (3) are formulated into an injection drug in accordance with a usual method for preparation of an injection drug.

Formulation Example 5 (ointment for external skin application)

(1) Compound No. 44 5g
(2) White vaseline 25 g
(3) Stearyl alcohol 22 g
(4) Propylene glycol 12 g
(5) Sodium lauryl sulfate 1.5 g
(6) Ethyl para-hydroxybenzoate 0.025 g
(7) Propyl para-hydroxybenzoate 0.015 g
(8) Purified water 100 g The components (1) to (8) are formulated into an ointment for external skin application by a usual method for preparation of an ointment.

Now, specific Examples for the preparation of the compounds of the present invention will be described.

PREPARATION EXAMPLE 1

Preparation of 2-tert-butyl-4-cyano-5-(4-pyridylmethylamino)pyridazin-3-(2H)-one (Compound No. 21)

(1) Into 300 ml of carbon tetrachloride, 22 g of 2-tert-butyl-5-chloro-4-methylpyridazin-3-(2H)-one, 78 g of N-bromosuccinimide and 4 g of benzoyl peroxide were added and reacted for 8 hours under irradiation with light and under heating and refluxing. Then, 78 g of N-bromosuccinimide and 3 g of benzoyl peroxide were added thereto. Further, ten hours later, 78 g of N-bromosuccinimide and 4 g of benzoyl peroxide were added thereto, and the mixture was reacted in the same manner for 14 hours and then left to cool. Insoluble matters were filtered off, and the filtrate was concentrated. The residual oil was subjected to column chromatography. Using an eluent (n-hexane:ethyl acetate=30:1), 27.4 g of 2-tert-butyl-5-chloro-4-dibromomethylpyridazin-3-(2H)-one having a melting point of from 98° to 99° C., was obtained.

(2) Into 300 ml of a 2-methoxyethanol solution of 27.4 g of 2-tert-butyl-5-chloro-4-dibromomethylpyridazin-3-(2H)-one, 200 ml of an aqueous solution of 39 g of silver nitrate was dropwise added at 10° C. over a period of 10 minutes, and the mixture was reacted for one hour under heating and refluxing. After cooling, insoluble matters were filtered off, and 500 ml of benzene was added to the filtrate. The mixture was washed with water, and the extract layer was dried over anhydrous sodium sulfate. The benzene was distilled off under reduced pressure to obtain 12.2 g of 2-tert-butyl-5-chloro-4-formylpyridazin-3-(2H)-one having a melting point of from 61° to 66° C.

(3) 25 ml of an aqueous solution of 2.5 g of hydroxyl amine hydrochloride and 2.5 g of potassium carbonate was stirred at room temperature for 10 minutes. Then, 60 ml of methanol was added thereto, and 15 ml of a methanol solution of 6.44 g of 2-tert-butyl-5-chloro-4-formylpyridazin-3-(2H)-one was dropwise added thereto at room temperature over a period of 10 minutes. The mixture was stirred for 20 minutes and then cooled with ice, and the precipitate was collected by filtration. From the filtrate, methanol was distilled off under reduced pressure, and the precipitate was collected by filtration and combined with the previously collected precipitate. The combined precipitate was thoroughly washed with water and dried under suction to obtain 6.43 g of 2-tert-butyl-5-chloro-4-hydroxyiminomethylidenylpyridazin-3-(2H)-one having a melting point of from 168° to 171° C.

(4) Into a 100 ml of a diethyl ether solution of 3.2 g of 2-tert-butyl-5-chloro-4-hydroxyiminomethylidenylpyridazin-3-(2H)-one, 10 ml of thionyl chloride was dropwise added under cooling with ice, and the mixture was stirred at room temperature for 40 minutes. Under cooling with ice, 100 ml of a saturated sodium chloride aqueous solution was gradually added thereto, and then the mixture was stirred for 10 minutes. The mixture was transferred to a separatory funnel, and ice pieces and 100 ml of diethyl ether were added thereto, followed by shaking. The extract layer was further washed with a saturated sodium chloride aqueous solution and then dried over anhydrous sodium sulfate. Diethyl ether was distilled off under reduced pressure, and the obtained powder was subjected to column chromatography. Using an eluent (n-hexane:ethyl acetate=9:1), 2.5 g of 2-tert-butyl-5-chloro-4-cyanopyridazin-3-(2H)-one having a melting point of from 85° to 87° C., was obtained.

(5) Into a 30 ml of ethanol solution of 2.1 g of 2-tert-butyl-5-chloro-4-cyanopyridazin-3-(2H)-one and 1.0 g of triethylamine, 1.1 g of 4-picolylamine was dropwise added under cooling with ice over a period of 5 minutes. Then, the mixture was stirred at room temperature for two hours and then concentrated. The mixture was extracted with ethyl acetate, and the extract was washed twice with a saturated sodium chloride aqueous solution and then dried. Ethyl acetate was distilled off under reduced pressure, and the residue thereby obtained was subjected to column chromatography. Using an eluent (ethyl acetate:methanol=20:1), 2.5 g of the desired product (Compound No. 21) having a melting point of from 174 to 175° C., was obtained.

PREPARATION EXAMPLE 2

Preparation of 2-tert-butyl-5-(4-pyridylmethylamino)-4-methoxyiminomethylidenylpyridazin-3-(2H)-one (Compound No. 16)

(1) 7 ml of an aqueous solution of 0.5 g of 0-methylhydroxylamine hydrochloride and 0.41 g of anhydrous potassium carbonate, was stirred at room temperature for 5 minutes, and then 20 ml of methanol was added thereto. Then, 5 ml of a methanol solution of 1.07 g of 2-tert-butyl-5-chloro-4-formylpyridazin-3-(2H)-one obtained in Preparation Example 1 (2), was gradually dropwise added at room temperature. After completion of the dropwise addition, stirring was continued at room temperature for 20 minutes. Then, the mixture was cooled with ice and the precipitate was collected by filtration. From the filtrate, methanol was distilled off, and the residue was extracted with ethyl acetate and washed once with water. The extract layer was dried over anhydrous sodium sulfate, and 1.3 g of the concentrated residual oil was subjected to column chromatography. Using an eluent (n-hexane:ethyl acetate=13:1), 0.89 g of 2-tert-butyl-5-chloro-4-methoxyiminomethylidenylpyridazin-3-(2H)-one having a melting point of from 74° to 76° C., was obtained.

(2) Into 20 ml of an absolute ethanol solution of 0.73 g of 2-tert-butyl-5-chloro-4-methoxyiminomethylidenylpyridazin-3-(2H)-one and 0.33 g of 4-picolylamine, 0.33 g of triethylamine was gradually dropwise added under cooling with ice, and the mixture was reacted for 6 hours under heating and refluxing. After cooling, 100 ml of ethyl acetate was added thereto, and the mixture was washed with water and further with a saturated sodium chloride aqueous solution. Then, the extract layer was dried over anhydrous sodium sulfate. 1.1 g of an oil obtained by concentration under reduced pressure, was dissolved in a small amount of hot acetone, and the solution was subjected to column chromatography. Using an eluent (ethyl acetate), 0.35 g of the desired product (Compound No. 16) having a melting point of from 152° to 154° C., was obtained.

PREPARATION EXAMPLE 3

Preparation of 2-tert-butyl-4-methoxycarbonyl-5-(4-pyridylmethylamino)pyridazin-3-(2H)-one (Compound No. 22)

(1) Into 30 ml of a methanol solution of 1.15 g of 2-tert-butyl-5-chloro-4-hydroxyiminomethylidenylpyridazin-3-(2H)-one obtained in Preparation Example 1 (3) and 15 mg of selenium dioxide (95% product), 2 ml of a 30% hydrogen peroxide aqueous solution was dropwise added with stirring at room temperature. Then, the mixture was reacted for one hour under heating and refluxing. After cooling, methanol was distilled off under reduced pressure, and 100 ml of methylene chloride and 100 ml of water were added, followed by shaking. The extract layer was dried over anhydrous sodium sulfate and then distilled under reduced pressure. The residue was subjected to column chromatography. Using an eluent (n-hexane:ethyl acetate=15:1), 0.25 g of 2-tert-butyl-5-chloro-4-methoxycarbonylpyridazin-3-(2H)-one having a melting point of from 101 to 102° C., was obtained.

(2) 7 ml of an absolute ethanol solution of 170 mg of 2-tert-butyl-5-chloro-4-methoxycarbonylpyridazin-3-(2H)-one, 76 mg of 4-picolylamine and 80 mg of triethylamine, was reacted for 4 hours under heating and refluxing and then left to cool. Ethanol was distilled off under reduced pressure, and 0.3 g of the obtained oil was subjected to column chromatography. Using an eluent (ethyl acetate:methanol= 20:1), 0.13 g of the desired product (Compound No. 22) having a melting point of from 99° to 100° C., was obtained.

PREPARATION EXAMPLE 4

Preparation of 2-tert-butyl-4-(4-methyl-1,3-dioxan-2-yl)-5-(4-pyridylmethylamino)pyridazin-3-(2H)-one (Compound No. 44)

(1) 50 ml of a dry benzene solution of 4.3 g of 2-tert-butyl-5-chloro-4-formylpyridazin-3-(2H)-one obtained in Preparation Example 1 (2), 18 g of 1,3-butanediol and 0.2 g of p-toluene sulfonic acid, was reacted for two hours under heating and refluxing by means of a Dean Stark trap. After cooling, 200 ml of benzene was added thereto, and the mixture was washed twice with water and then dried over anhydrous sodium sulfate and distilled under reduced pressure. 7 g of the residue thus obtained was subjected to column chromatography. Using an eluent (n-hexane:ethyl acetate=6:1), 4.6 g of oily 2-tert-butyl-5-chloro-4-(4-methyl-1,3-dioxan-2-yl)pyridazin-3-(2H)-one was obtained.

(2) Into 20 ml of an absolute ethanol solution of 2.7 g of 4-picolylamine, 20 ml of an absolute ethanol solution of 3.4 g of 2-tert-butyl-5-chloro-4-(4-methyl-1,3-dioxan-2-yl)pyridazin-3-(2H)-one was dropwise added at room temperature. The mixture was reacted overnight under heating and refluxing and then left to cool. Ethanol was distilled off under reduced pressure, and then 150 ml of ethyl acetate was added to the residue. The mixture was washed with water and dried over anhydrous sodium sulfate. Then, the solvent was distilled off. The residue was subjected to column chromatography. Using an eluent (ethyl acetate:methanol= 30:1 to 12:1), 1.2 g of the desired product (Compound No. 44) having a melting point of from 150° to 153° C. and 0.18 g of amorphous 4-tert-butyl-5-(4-pyridylmethylamino)-4-(4-pyridylmethyliminomethylidenyl)pyridazin-3-(2H) -one (Compound No. 2) as a by-product, were obtained.

PREPARATION EXAMPLE 5

Preparation of 2-tert-butyl-4-formyl-5-(4-pyridylmethylamino) pyridazin-3-(2H)-one (Compound No. 24)

(1) Into 3 ml of a trifluoroacetic acid solution of 0.22 g of 2-tert-butyl-4-(4-methyl-1,3-dioxan-2-yl)-5-(4-pyridylmethylamino)pyridazin-3-(2H)-one obtained in Preparation Example 4 (2), 0.5 ml of deionized water was thoroughly dropwise added at room temperature. The mixture was stirred at room temperature for one hour. Then, 80 ml of ethyl acetate was added to the system, and the mixture was washed with a saturated sodium chloride aqueous solution. Then, the ethyl acetate layer was dried over anhydrous sodium sulfate, and the solvent was distilled off. The residue was subjected to column chromatography, and using an eluent (ethyl acetate:methanol=40:1), 0.15 g of the desired product (Compound No. 24) having a melting point of from 90° to 93° C. was obtained.

PREPARATION EXAMPLE 6

Preparation of 2-tert-butyl-4-difluoromethyl-5-(4-pyridylmethylamino)pyridazin-3-(2H)-one (Compound No. 12)

(1) Into 30 ml of a dry benzene solution of 2.1 g of 2-tert-butyl-5-chloro-4-formylpyridazin-3-(2H)-one obtained in Preparation Example 1 (2), 3.5 g of DAST (Diethylaminosulfur trifluoride) reagent was dropwise added under cooling with ice, and the mixture was stirred for one hour. The solvent was distilled off, and the residue was subjected to column chromatography. Using an eluent (n-hexane:methyl acetate=15:1), 1.8 g of 2-tert-butyl-5-chloro-4-difluoromethylpyridazin-3-(2H)-one having a melting point of from 69° to 70° C., was obtained.

(2) 20 ml of an absolute ethanol solution of 0.71 g of 2-tert-butyl-5-chloro-4-difluoromethylpyridazin-3-(2H)-one, 0.33 g of 4-picolylamine and 0.33 g of triethylamine, was reacted for 5 hours under heating and refluxing and left to cool. Then, the mixture was extracted with ethyl acetate, then washed with water and a saturated sodium chloride aqueous solution and then dried over anhydrous sodium sulfate. The solvent was distilled off. The residue was subjected to column chromatography, and using an eluent (n-hexane:ethyl acetate=1:2), 0.32 g of the desired product (Compound No. 12) having a melting point of from 142° to 143° C. and 0.04 g of amorphous 2-tert-butyl-5-(4-pyridylmethylamino)-4-(4-pyridylmethyliminomethylidenyl)pyridazin-3-(2H)-one (Compound No. 2) as a by-product, were obtained.

PREPARATION EXAMPLE 7

Preparation of 4-cyano-2-ethyl-5-(4-pyridylmethylamino)pyridazin-3-(2H)-one (Compound No. 47)

(1) 8.5 g of 4,5-dibromo-2-ethylpyridazin-3-(2H)-one, 1.6 g of sodium cyanide, 2.7 g of copper cyanide and 100 ml of anhydrous dimethylformamide were stirred under heating at from 90° to 100° C. for 3 hours and further at 110° C. for 3 hours and then left to cool. After cooling the mixture to room temperature, the mixture was introduced into 300 ml of water and 400 ml of ethyl acetate with stirring. Ten minutes later, insoluble powder was filtered off by means of celite. To the filtrate, 200 ml of benzene was added, and the mixture was thoroughly shaked in a separatory funnel and then left to stand overnight. The organic layer was dried over anhydrous sodium sulfate, and then the solvent was distilled off. The residue was subjected to column chromatography. Using an eluent (n-hexane:ethyl acetate=7:1 to 4:1), 0.2 g of 5-bromo-4-cyano-2-ethylpyridazin-3-(2H)-one having a melting point of from 77 to 80° C. and 1.9 g of 4,5-dicyano-2-ethylpyridazin-3-(2H)-one having a melting point of from 93.5 to 94° C., were obtained.

(2) Into 5 ml of an absolute ethanol solution of 0.16 g of 4-picolylamine, 5 ml of an absolute ethanol suspension of 0.11 g of 5-bromo-4-cyano-2-ethylpyridazin-3-(2H)-one, was dropwise added under cooling with ice over a period of 20 minutes. After completion of the dropwise addition, the mixture was reacted at room temperature for one hour. Then, ethanol was distilled off under reduced pressure, and the residue was extracted with ethyl acetate. The extract was washed once with water and dried over anhydrous sodium sulfate and then concentrated. To the residue, n-hexane and ethyl ether were added in a small amount for crystallization. The crystals were collected by filtration and dried to obtain 77 mg of the desired product (Compound No. 47) having a melting point of from 193° to 195° C.

(3) Into 305 ml of an absolute ethanol solution of 1.9 g of 4-picolylamine, 30 ml of an absolute ethanol suspension of 1.4 g of 4,5-dicyano-2-ethylpyridazin-3-(2H)-one was dropwise added under cooling with ice over a period of 30 minutes. After completion of the dropwise addition, the mixture was reacted at room temperature overnight. Then, ethanol was distilled off under reduced pressure. To the residue, 250 ml of ethyl acetate and 100 ml of water were added, followed by shaking. The ethyl acetate layer was dried over anhydrous sodium sulfate and then distilled under reduced pressure. The residue was subjected to column chromatography, and using an eluent (ethyl acetate:methanol=40:1), 0.3 g of the desired product (Compound No. 47) was obtained.

PREPARATION EXAMPLE 8

Preparation of 2-tert-butyl-4-hydroxy-5-(4-pyridylmethylamino)pyridazin-3-(2H)-one (Compound No. 45)

(1) Into 40 ml of an absolute methanol solution of 5.3 g of 2-tert-butyl-4-hydroxy-5-nitropyridazin-3-(2H)-one, 0.5 g of palladium-carbon (containing 5% of Pd) was added in a few times at room temperature with stirring. Then, catalytic reduction was carried out overnight under hydrogen gas pressure. After completion of the reaction, the palladium-carbon was separated by filtration with celite and washed a few times with absolute methanol. The methanol was combined with the filtrate, followed by distillation under reduced pressure to obtain 4.4 g of powdery 5-amino-2-tert-butyl-4-hydroxypyridazin-3-(2H)-one.

(2) 50 ml of a dry benzene solution of 3.1 g of 5-amino-2-tert-butyl-4-hydroxypyridazin-3-(2H)-one, 1.9 g of isonicotinaldehyde and 0.17 g of p-toluene sulfonic acid, was reacted for 1.5 hours under heating and refluxing by means of a Dean Stark trap. After cooling, 100 ml of ethyl acetate was added to the reaction mixture, and the mixture was washed with water and then with a saturated sodium chloride aqueous solution, and then dried over anhydrous sodium sulfate. The solvent was distilled off under reduced pressure to obtain 3.3 g of 2-tert-butyl-4-hydroxy-5-(4-pyridylimino)pyridazin-3-(2H)-one as a powder.

(3) Into 10 ml of an absolute methanol solution of 1.36 g of 2-tert-butyl-4-hydroxy-5-(4-pyridylimino)pyridazin-3-(2H)-one, 0.11 g of sodium borohydride was added in a few times under cooling with ice. Then, the mixture was stirred at room temperature for two hours. Methanol was distilled off under reduced pressure, and then 100 ml of water and 150 ml of ethyl acetate were added thereto, followed by shaking. The insoluble powder was collected by filtration and washed with deionized water and then with diethyl ether (containing a small amount of ethyl acetate), and then dried under suction to obtain 0.71 g of the desired product (Compound No. 45) having a melting point of from 243° to 245° C.

PREPARATION EXAMPLE 9

Preparation of 2-tert-butyl-4-methylthio-5-(4-pyridylmethylamino)pyridazin-3-(2H)-one (Compound No. 7)

(1) Into 20 ml of a dioxane solution of 2.31 g of 2-tert-butyl-4-chloro-5-nitropyridazin-3-(2H)-one, 5 ml of an aqueous solution of 0.7 g of sodium methylmercaptan was dropwise added over a period of 4 minutes under cooling with ice. The mixture was stirred at room temperature for 10 minutes and then extracted with ethyl acetate. The extract was washed with water and then with saturated sodium chloride aqueous solution, and then it was dried over anhydrous sodium sulfate and concentrated. The residual oil was subjected to column chromatography, and using an eluent (n-hexane:ethyl acetate=20:1), 1.5 g of oily 2-tert-butyl-4-methylthio-5-nitropyridazin-3-(2H)-one was obtained.

(2) Into 10 ml of an acetic acid solution of 1.45 g of 2-tert-butyl-4-methylthio-5-nitropyridazin-3-(2H)-one, 1.33 g of reduced iron was gradually added in a few times over a period of 10 minutes with stirring at 65° C. During the addition, the temperature of the system was maintained from 65° to 75° C. After completion of the addition, the mixture was stirred at a temperature of from 65° to 70° C. for one hour and then left to cool. 100 ml of ethyl acetate was added thereto, and the mixture was filtered through celite. The filtrate was washed twice with water and then with a dilute potassium carbonate aqueous solution, and then it was dried over anhydrous sodium sulfate and concentrated to obtain 1.0 g of 5-amino-2-tert-butyl-4-methylthiopyridazin-3-(2H)-one as a residual powder.

(3) 40 ml of a dry benzene solution of 1.5 g of 5-amino-2-tert-butyl-4-methylthiopyridazin-3-(2H)-one, 0.75 g of isonicotinaldehyde and 0.08 g of p-toluene sulfonic acid, was reacted for 6 hours under heating and refluxing by means of a Dean Stark trap. The mixture was extracted with ethyl acetate, and the extract was washed twice with water, then dried over anhydrous sodium sulfate and concentrated to obtain 2.1 g of crude powder of 2-tert-butyl-4-methylthio-5-(4-pyridylimino)pyridazin-3-(2H)-one as a residue.

(4) Into 7 ml of an absolute methanol solution of 0.91 g of 2-tert-butyl-4-methylthio-5-(4-pyridylimino)pyridazin-3-(2H)-one, 0.07 g of sodium borohydride was added in a few times under cooling with ice. The mixture was stirred for 20 minutes. Methanol was distilled off under reduced pressure, and the residue was extracted with ethyl acetate. The extract was washed twice with water and dried over anhydrous sodium sulfate. Then, ethyl acetate was distilled off under reduced pressure, and the residue was subjected to column chromatography. Using an eluent (n-hexane:ethyl acetate=

1:9), 0.58 g of the desired product (Compound No. 7) having a melting point of 107° to 110° C. was obtained.

PREPARATION EXAMPLE 10

Preparation of 2-tert-butyl-4-methanesulfinyl-5-(4-pyridylmethylamino)pyridazin-3-(2H)-one
(Compound No. 8)

Into 10 ml of a methylene chloride solution of 0.38 g of 2-tert-butyl-4-methylthio-5-(4-pyridylmethylamino) pyridazin-3-(2H)-one obtained in Preparation Example 9, 0.27 g of m-chloroperbenzoic acid was gradually added at room temperature, and then the mixture was reacted at room temperature for 3 hours. Methylene chloride was added to bring the total volume to 100 ml. The mixture was washed with water, then dried over anhydrous sodium sulfate and distilled under reduced pressure. The residue was subjected to column chromatography, and using an eluent (ethyl acetate:methanol=20:1), 0.22 g of the desired product (Compound No. 8) having a melting point of from 131° to 137° C., was obtained.

PREPARATION EXAMPLE 11

Preparation of 2-tert-butyl-4-methanesulfonyl-5-(4-pyridylmethylamino)pyridazin-3-(2H)-one
(Compound No. 9)

Into 5 ml of a methylene chloride solution of 0.09 g of 2-tert-butyl-4-methanesulfinyl-5-(4-pyridylmethylamino) pyridazin-3-(2H)-one obtained in Preparation Example 10, 0.08 g of m-chloroperbenzoic acid was gradually added at room temperature. Then, the mixture was reacted at room temperature for 3 hours. The mixture was extracted with a total amount of 50 ml of methylene chloride, and the extract was washed once with water and dried over anhydrous sulfate. The solvent was distilled off under reduced pressure. The residual powder was subjected to column chromatography, and using an eluent (ethyl acetate:methanol=5:1), 0.04 g of the desired product (Compound No. 9) having a melting point of from 206° to 209° C., was obtained.

PREPARATION EXAMPLE 12

Preparation of 4-amino-2-tert-butyl-5-(4-pyridylmethylamino)pyridazin-3-(2H)-one
(Compound No. 10)

(1) 6.95 g of 2-tert-butyl-4-chloro-5-nitropyridazin-3-(2H)-one and 50 ml of 28% aqueous ammonia were mixed, sealed and reacted for 5 hours in an oil bath of 110° C. After cooling, the precipitate was collected by filtration and washed a few times with water and then dried to obtain 5.97 g of 4-amino-2-tert-butyl-5-nitropyridazin-3-(2H)-one.

(2) Into 150 ml of an absolute methanol solution of 10.8 g of 4-amino-2-tert-butyl-5-nitropyridazin-3-(2H)-one, 1.1 g of palladium-carbon (containing 5% of Pd) was added in a few times with stirring at room temperature. Then, catalytic reduction was carried out overnight under hydrogen gas pressure. After completion of the reaction, palladium-carbon was separated with celite and washed a few times with absolute methanol. Then, methanol was combined with the filtrate, and the mixture was distilled under reduced pressure to obtain 9.3 g of powdery 4,5-diamino-2-tert-butylpyridazin-3-(2H)-one.

(3) 30 ml of a dry benzene solution of 1.8 g of 4,5-diamino-2-tert-butylpyridazin-3-(2H)-one, 1.1 g of isonicotinaldehyde and 0.1 g of p-toluene sulfonic acid, was reacted for 8 hours under heating and refluxing by means of a Dean Stark trap. After cooling, 100 ml of ethyl acetate was added to the reaction mixture. The mixture was washed with water and then with a saturated sodium chloride aqueous solution, then dried over anhydrous sodium sulfate and distilled under reduced pressure to obtain 2.3 g of a powder of 4-amino-2-tert-butyl-5-(4-pyridylimino)pyridazin-3-(2H)-one as the residue.

(4) Into 150 ml of an absolute methanol solution of 10.8 g of 4-amino-2-tert-butyl-5-(4-pyridylimino)pyridazin-3-(2H)-one, 0.76 g of sodium borohydride was added in a few times under cooling with ice. Then, the mixture was stirred at room temperature for 40 minutes, and the 0.76 g of sodium borohydride was further added thereto. The mixture was stirred for 0.5 hour. Methanol was distilled off under reduced pressure, and 200 ml of water and 400 ml of ethyl acetate were added to the residue, followed by shaking. The insoluble powder was collected by filtration. The organic layer in the filtrate was dried over anhydrous sodium sulfate and distilled under reduced pressure to obtain 4.7 g of a residue. The residue was combined to the previously obtained insoluble powder, and the mixture was thoroughly washed with a solvent mixture comprising 150 ml of n-hexane and 50 ml of methylene chloride, and then dried to obtain 8.7 g of the desired product (Compound No. 10) having a melting point of from 219° to 225° C.

PREPARATION EXAMPLE 13

Preparation of 2-tert-butyl-4-N,N-bis (methanesulfonyl)amino-5-(4-pyridylmethylamino) pyridazin-3-(2H)-one (Compound No. 30)

Into 20 ml of a dry benzene solution of 0.55 g of 4-amino-2-tert-butyl-5-(4-pyridylmethylamino)pyridazin-3-(2H)-one and 0.46 g of methanesulfonyl chloride, triethyl amine was slowly dropwise added under cooling with ice. The mixture was reacted at room temperature overnight. Then, ethyl acetate was added thereto for extraction. The extract was washed with water and then with a saturated sodium chloride aqueous solution. It was then dried over anhydrous sodium sulfate and concentrated, and the residue was subjected to column chromatography. Using an eluent (n-hexane:ethyl acetate=1:5), 0.17 g of the desired product (Compound No. 30) having a melting point of from 227° to 230° C. was obtained.

PREPARATION EXAMPLE 14

Preparation of 2-tert-butyl-4-propionylamide-5-(4-pyridylmethylamino)pyridazin-3-(2H)-one
(Compound No. 28)

Into 10 ml of a tetrahydrofuran solution of 0.41 g of 4-amino-2-tert-butyl-5-(4-pyridylmethylamino)pyridazin-3-(2H)-one, 0.15 g of propionyl chloride was dropwise added with stirring at room temperature, and the mixture was reacted overnight. Then, it was reacted at 40° C. for one hour, and then 20 ml of methylene chloride was added to the system. Insoluble powder, etc. were filtered. The filtration product and the filtrate were put together into a 0.2N-KOH aqueous solution (about 10° C.). After thoroughly mashing the mixture, the mixture was extracted with 90 ml of methylene chloride and dried over anhydrous sodium sulfate. The concentrated residue was subjected to column chromatography. Using an eluent (ethyl acetate:methanol= 15:1), 0.24 g of the desired product (Compound No. 28) having a melting point of 119° to 122° C., was obtained.

PREPARATION EXAMPLE 15

Preparation of 4-benzenesulfonylamino-2-tert-butyl-5-(4-pyridylmethylamino)pyridazin-3-(2H)-one
(Compound No. 32)

Into 6 ml of a pyridine solution of 0.55 g of 4-amino-2-tert-butyl-5-(4-pyridylmethylamino)pyridazin-3-(2H)-one, 0.36 g of benzenesulfonyl chloride was dropwise added at room temperature. The mixture was reacted overnight, and 80 ml of water and 100 ml of methylene chloride were added to the system. The mixture was adjusted to pH4 with dilute hydrochloric acid under cooling with ice, and then stirred for 20 minutes. The organic layer was dried over anhydrous sodium sulfate and then concentrated. To the residue, 4 ml of ethyl acetate was added, and the mixture was mashed, whereupon crystals were collected by filtration. The obtained crystals were subjected to column chromatography, and using an eluent (n-hexane:ethyl acetate=1:5), 0.30 g of the desired product (Compound No. 32) having a melting point of from 189° to 190° C., was obtained.

PREPARATION EXAMPLE 16

Preparation of 2-tert-butyl-4-methyl-5-(4-pyridylcarbonylamino)pyridazin-3-(2H)-one
(Compound No. 1)

0.72 of 5-amino-2-tert-butyl-4-methylpyridazin-3-(2H)-one, 0.57 g of 4-pyridylcarbonyl chloride, 0.55 g of anhydrous potassium carbonate and 30 ml of dry acetone were mixed and vigorously stirred at room temperature for 40 minutes. Acetone was distilled off under reduced pressure, and the residue was extracted with 150 ml of methylene chloride and washed twice with water. Then, It was dried over anhydrous sodium sulfate and concentrated. The residue thereby obtained was subjected to column chromatography, and using an eluent (n-hexane:ethyl acetate=1:2), 0.56 g of the desired product (Compound No. 1) having a melting point of from 206° to 207° C., was obtained.

PREPARATION EXAMPLE 17

Preparation of 4-hydroxymethyl-2-methyl-5-(4-pyridylmethylamino)pyridazin-3-(2H)-one
(Compound No. 70)

(1) Into 200 ml of absolute ether, 100 ml of a 3.0M diethyl ether solution of methyl magnesium bromide was added, and 92 ml of an absolute ether solution of 38.25 g of 4,5-dibromo-2-methylpyridazin-3-(2H)-one was dropwise added under cooling with ice at from 0° to 10° C. After completion of the dropwise addition, the mixture was stirred for 40 minutes at a temperature of from 5° to 10° C. Then, 65 ml of 6N hydrochloric acid was added to the reaction solution. Then, 300 ml of ethyl ether was added thereto, and the mixture was subjected to liquid separation. The ether layer was washed with a saturated sodium chloride aqueous solution and then dried over anhydrous sodium sulfate. The solvent was distilled off under reduced pressure, and the residue was subjected to silica gel column chromatography, and from a fraction of n-hexane:ethyl acetate=4:1, 7.0 g of a 7:3 mixture of 5-bromo-2,4-dimethylpyridazin-3-(2H)-one and 4,5-dibromo-2-methylpyridazin-3-(2H)-one, was obtained.

(2) Into 40 ml of carbon tetrachloride, 7.0 g of the mixture of 5-bromo-2,4-dimethylpyridazin-3-(2H)-one and 4,5-dibromo-2-methylpyridazin-3-(2H)-one obtained in the above step (1), 3.50 g of N-bromosuccinimide and 0.19 g of benzoyl peroxide were added, and the mixture was reacted for 3 hours under heating and refluxing under irradiation with light. After cooling, precipitated succinimide was filtered off, and the filtrate was washed with water and then dried over anhydrous sodium sulfate. The solvent was distilled off under reduced pressure, and the residue was subjected to silica gel column chromatography. From a fraction of n-hexane:ethyl acetate=4:1, 6.76 g of a 1:1 mixture of 5-bromo-4-bromomethyl-2-methylpyridazin-3-(2H)-one and 4,5-dibromo-2-methylpyridazin-3-(2H)-one, was obtained.

(3) 6.76 g of the mixture of 5-bromo-4-bromomethyl-2-methylpyridazin-3-(2H)-one and 4,5-dibromo-2-methylpyridazin-3-(2H)-one obtained in the above step (2) and 6.24 g of calcium carbonate were added to a mixture of 67 ml of dioxane and 67 ml of water, and the mixture was heated and refluxed for 5 hours. After completion of the reaction, dioxane was distilled off under reduced pressure, and to the residue, 44 ml of 3N hydrochloric acid was added. The mixture was extracted with 120 ml of dichloromethane. The dichloromethane layer was dried over anhydrous sodium sulfate, and then the solvent was distilled off. The residue was subjected to silica gel column chromatography, and from a fraction of n-hexane:ethyl acetate=2:1, 2.05 g of 5-bromo-4-hydroxymethyl-2-methylpyridazin-3-(2H)-one having a melting point of from 79° to 80° C., was obtained.

(4) 1.0 g of 5-bromo-4-hydroxymethyl-2-methylpyridazin-3-(2H)-one obtained in the above step (3) and 1.48 g of 4-picolylamine were added to 10 ml of dioxane, and the mixture was heated and refluxed for 18 hours. The precipitate was filtered off, and the filtrate was concentrated. The residue was subjected to silica gel column chromatography, and from a fraction of ethyl acetate:methanol=4:1, 0.50 g of the desired compound (Compound No. 70) having a melting point of from 135° to 137° C., was obtained.

PREPARATION EXAMPLE 18

Preparation of 2-methyl-4-(N-methyl)acetylamino-5-(4-pyridylmethylamino)pyridazin-3-(2H)-one
(Compound No. 69)

(1) Into 50 ml of a dry tetrahydrofuran solution of 5.88 g of 5-chloro-4-methylamino-2-methylpyridazin-3-(2H)-one and 6.1 g of hexamethylphosphoric triamide, 24.8 ml of a 1.64 mol/l hexane solution of n-butyllithium was dropwise added over a period of 5 minutes at −20° C. Then, the mixture was stirred at a temperature of from −20° C. to 5° C. (mainly from −10° C. to 0° C.) for 1.5 hours. At 0° C., 4.0 g of acetyl chloride was gradually added thereto over a period of 5 minutes, and then the mixture was stirred at room temperature overnight. Tetrahydrofuran was distilled off for concentration, and 200 ml of ethyl acetate was added to the residue. The extract was washed twice with water and then dried over anhydrous sodium sulfate. The solvent was distilled off under reduced pressure. The residue was subjected to column chromatography, and using an eluent (n-hexane:ethyl acetate~2:1 to ethyl acetate only), 2.2 g of 5-chloro-2-methyl-4-(N-methyl)acetylaminopyridazin-3-(2H)-one having a melting point of from 126° to 134° C., was obtained.

(2) Into 30 ml of a dry methoxyethanol solution of 1.72 g of 5-chloro-2-methyl-4-(N-methyl)acetylaminopyridazin-3-(2H)-one, 2.6 g of 4-picolylamin was dropwise added at room temperature. Then, the mixture was reacted overnight under heating and refluxing. After cooling, the solvent was distilled off under reduced pressure, and 100 ml of ethyl acetate was added to the residue. The extract was washed with water and dried over anhydrous sodium sulfate. Then, the solvent was distilled off, and the residue was subjected to column chromatography. Using an eluent (ethyl acetate:methanol=4:1 to 3:1), 1.0 g of the desired product (Compound No. 69) having a melting point of from 177° to 179° C., was obtained.

PREPARATION EXAMPLE 19

Preparation of 4-methoxymethyl-2-methyl-5-(N-methyl-4-pyridylmethylamino)pyridazin-3-(2H)-one (Compound No. 73)

(1) Into 225 ml of a 3.0M diethyl ether solution of methyl magnesium bromide, 170 ml of an absolute ether solution of 74.40 g of 4,5-dichloro-2-tert-butyl-pyridazin-3-(2H)-one was dropwise added under cooling with ice at a temperature of from 5° to 10° C. After completion of the dropwise addition, the mixture was stirred at a temperature of from 5° to 10° C. for two hours. Then, 158 ml of 6N hydrochloric acid was added to the reaction solution, and then 600 ml of diethyl ether was added thereto for liquid separation. The ether layer was washed with a saturated sodium chloride aqueous solution and then dried over anhydrous sodium sulfate. The solvent was distilled off under reduced pressure, and the residue was subjected to silica gel column chromatography. From a fraction of n-hexane:ethyl acetate=9:1, 24.45 g of oily 2-tert-butyl-5-chloro-4-methylpyridazin-3-(2H)-one, was obtained.

(2) 12.02 g of 2-tert-butyl-5-chloro-4-methylpyridazin-3-(2H)-one obtained in the above step (1) was dissolved in 21.9 ml of concentrated sulfuric acid. To this solution, 7.9 ml of fuming nitric acid was dropwise added at a temperature of not higher than 30° C. After completion of the dropwise addition, the mixture was stirred at room temperature for one hour. After completion of the reaction, the reaction solution was poured into 180 ml of ice water, whereupon precipitated crystals were collected by filtration, washed with water and dried under reduced pressure to obtain 5.42 g of 5-chloro-4-methylpyridazin-3-(2H)-one having a melting point of from 118° to 119° C.

(3) Into 79 ml of an N,N-dimethylformamide solution of 7.85 g of 5-chloro-4-methylpyridazin-3-(2H)-one obtained in the above step (2), 2.4 g of sodium hydride (containing 40% mineral oil) was added at room temperature. After the addition, the mixture was stirred for 30 minutes. Then, 9.25 g of methyl iodide was dropwise added thereto at a temperature of not higher than 20° C. After completion of the dropwise addition, the mixture was stirred at room temperature for two hours. After completion of the reaction, 200 ml of water and 16 ml of 10% hydrochloric acid were added to the reaction mixture, and the mixture was extracted with 200 ml of benzene. The benzene layer was dried over anhydrous sodium sulfate, and then the solvent was distilled off. The residue was subjected to silica gel column chromatography, and from a fraction of n-hexane:ethyl acetate=4:1, 5.41 g of 5-chloro-2,4-dimethylpyridazin-3-(2H)-one having a melting point of from 59° to 60° C., was obtained.

(4) Into 54 ml of carbon tetrachloride, 5.41 g of 5-chloro-2,4-dimethylpyridazin-3-(2H)-one obtained in the above step (3), 6.07 g of N-bromosuccinimide and 0.33 g of benzoyl peroxide were added, and the mixture was reacted for 6 hours under heating and refluxing under irradiation with light. After cooling, precipitated succinimide was filtered off, and the filtrate was washed with water and then dried over anhydrous sodium sulfate. The solvent was distilled off under reduced pressure, and the residue was subjected to silica gel column chromatography. From a fraction of n-hexane:ethyl acetate=4:1, 7.07 g of 4-bromomethyl-5-chloro-2-methylpyridazin-3-(2H)-one having a melting point of from 49° to 51° C., was obtained.

(5) 7.07 g of 4-bromomethyl-5-chloro-2-methylpyridazin-3-(2H)-one obtained in the above step (4) and 14.9 g of calcium carbonate were added to a mixed solution of 70 ml of dioxane and 70 ml of water, and the mixture was heated and refluxed for 6.5 hours. After completion of the reaction, dioxane was distilled off under reduced pressure, and to the residue, 100 ml of 3N hydrochloric acid was added. The mixture was extracted with 300 ml of dichloromethane. The dichloromethane layer was dried over anhydrous sodium sulfate, and then the solvent was distilled off under reduced pressure. The residue was subjected to silica gel column chromatography, and from a fraction of n-hexane:ethyl acetate=2:1, 4.31 g of 5-chloro-4-hydroxymethyl-2-methylpyridazin-3-(2H)-one having a melting point of from 60° to 61° C., was obtained.

(6) 4.31 g of 5-chloro-4-hydroxymethyl-2-methylpyridazin-3-(2H)-one obtained in the above step (5) and 8.0 g of 4-picolylamine were added to 43 ml of dioxane, and the mixture was heated and refluxed for 17 hours. After cooling, the precipitate was filtered off, and the filtrate was concentrated. The residue was subjected to silica gel column chromatography, and from a fraction of ethyl acetate:methanol=4:1, 1.83 g of 4-hydroxymethyl-2-methyl-5-(4-pyridylmethylamino)pyridazin-3-(2H)-one (Compound No. 70) having a melting point of from 135° to 137° C., was obtained.

(7) 1.58 g of 4-hydroxymethyl-2-methyl-5-(4-pyridylmethylamino)pyridazin-3-(2H)-one obtained in the above step (6) and 2.18 g of methyl iodide were dissolved in a mixed solution of 32 ml of tetrahydrofuran and 8 ml of N,N-dimethylformamide. Then, 0.56 g of sodium hydride (containing 40% of mineral oil) was added thereto under cooling with ice, and the mixture was stirred at a temperature of from 5° to 10° C. for one hour. After completion of the reaction, 50 ml of water was added, and the mixture was extracted with 180 ml of ethyl acetate. The ethyl acetate layer was dried over anhydrous sodium sulfate. Then, the solvent was distilled off under reduced pressure, and the residue was subjected to silica gel column chromatography. From a fraction of ethyl acetate:methanol=17:3, 0.83 g of the desired product (Compound No. 73) having a melting point of from 93° to 94° C., was obtained.

PREPARATION EXAMPLE 20

Preparation of 4-methoxymethyl-2-methyl-5-(4-pyridylmethylamino)pyridazin-3-(2H)-one (Compound No. 105)

(1) Into 120 ml of carbon tetrachloride, 14.26 g of 2-tert-butyl-5-chloro-4-methylpyridazin-(2H)-one, 12.6 g of N-bromosuccinimide and 0.69 g of benzoyl peroxide were added, and the mixture was reacted for 6 hours under heating and refluxing under irradiation with light. After cooling, precipitated succinimide was filtered off, and the filtrate was washed with water and dried over anhydrous sodium sulfate. The solvent was distilled off under reduced pressure, and the residue was subjected to silica gel column chromatography. From a fraction of n-hexane:ethyl acetate=9:1, 19.27 g of 2-tert-butyl-4-bromomethyl-5-chloropyridazin-3-(2H)-one having a melting point of from 99° to 100° C., was obtained.

(2) Into 75 ml of methanol, 0.41 g of metal sodium was added and dissolved, and then 5.00 g of 2-tert-butyl-4-bromomethyl-5-chloropyridazin-3-(2H)-one obtained in the above step (1) was added thereto. The mixture was stirred at room temperature for 1.5 hours, then further heated to 60° C. and reacted for 1.5 hours. After cooling, methanol was distilled off under reduced pressure, and the residue was extracted with 180 ml of ethyl acetate. The ethyl acetate layer was dried over anhydrous sodium sulfate, and then the solvent was distilled off under reduced pressure. The residue was subjected to silica gel column chromatography, and from a fraction of n-hexane:ethyl acetate=9:1, 2.55 g of oily 2-tert-butyl-5-chloro-4-methoxymethylpyridazin-3-(2H)-one was obtained.

(3) 4.4 g of 2-tert-butyl-5-chloro-4-methoxymethylpyridazin-3-(2H)-one obtained in the above step (2) was dissolved in 13.6 ml of concentrated sulfuric acid. To this solution, 2.4 ml of fuming nitric acid was dropwise added at a temperature of not higher than 30° C. After completion of the dropwise addition, the mixture was stirred at room temperature for two hours. After completion of the reaction, the reaction solution was poured into 60 ml of ice water, and the mixture was extracted with 180 ml of ethyl acetate. The ethyl acetate layer was dried over anhydrous sodium sulfate, and the solvent was distilled off under reduced pressure. The residue was subjected to silica gel column chromatography, and from a fraction of n-hexane:ethyl acetate=2:1, 2.17 g of 5-chloro-4-methoxymethylpyridazin-3-(2H)-one having a melting point of from 118° to 119° C., was obtained.

(4) Into 22 ml of an N,N-dimethylformamide solution of 2.17 g of 5-chloro-4-methoxymethylpyridazin-3-(2H)-one prepared in the above step (3), 0.55 g of sodium hydride (containing 40% of mineral oil) was added at room temperature. After the addition, the mixture was stirred for 30 minutes. Then, 2.12 g of methyl iodide was dropwise added thereto at a temperature of not higher than 20° C. After completion of the dropwise addition, the mixture was stirred at room temperature for one hour. After completion of the reaction, 70 ml of water and 4 ml of 10% hydrochloric acid were added to the reaction mixture, and the mixture was extracted with 70 ml of benzene. The benzene layer was dried over anhydrous sodium sulfate, and then the solvent was distilled off under reduced pressure. The residue was subjected to silica gel column chromatography, and from a fraction of n-hexane:ethyl acetate=3:1, 1.53 g of 5-chloro-2-methyl-4-methoxymethylpyridazin-3-(2H)-one having a melting point of from 47 to 49° C., was obtained.

(5) 1.53 g of 5-chloro-2-methyl-4-methoxymethylpyridazin-3-(2H)-one obtained in the above step (4) and 2.63 g of 4-picolylamine were added to 15 ml of dioxane, and the mixture was heated and refluxed for 24 hours. After cooling, the precipitate was filtered off, and the filtrate was concentrated. The residue was subjected to silica gel column chromatography, and from a fraction of ethyl acetate:methanol=9:1, 1.20 g of the desired product (Compound No. 105) was obtained as an oily substance.

Now, typical specific examples of the intermediate of the formula (II-4) of the present invention will be given in Table 1, and typical specific examples of the compound of the formula (I) of the present invention will be given in Table 2.

TEST EXAMPLE 1

A drug having a test compound dissolved in the form of its $Na^+$ salt or $Cl^-$ salt in saline or suspended in saline containing 0.5% by weight of carboxymethyl cellulose (manufactured by Nakalai Tesque K. K., hereinafter referred to simply as CMC), was intraperitonially injected to SD male rats of seven weeks old. Thirty minutes after the injection, lipopolysaccharide derived from *E. coli* (manufactured by Difco Company, Product No. 0127:B8) was intravenously injected into the tail vein of each rat so that the dose would be 10 mg/kg. One hour after the injection of the lipopolysaccharide, enteric hemorrhage of each rat was inspected, and the degree of hemorrhage was evaluated by the following ratings:

0: No hemorrhage

1: Slight hemorrhage

2: Slight subepithelial congestion

4: Subepithelial congestion over a wide range and slight submucous congestion

6: Submucous congestion over a wide range, flow out of blood from submucous tissues and necrosis For the control, the test was conducted in the same manner except that no test compound was added.

The inhibition rate was obtained by the following formula. The obtained results are shown in Table 3.

Inhibition rate $(\%)=(A-B)/A\times100$ where

A: rating of the control

B: rating of a rat administered with a test compound

TABLE 3

| Compound No. | Dose (mg/kg) | | | |
|---|---|---|---|---|
| | 100 | 50 | 25 | 12.5 |
| 1 | | | 96 | |
| 2 | | | 98 | 75 |
| 3 | | | | 95 |
| 4 | | | | 80 |
| 5 | | | | 43 |
| 6 | | | 30 | |
| 7 | | 100 | | 78 |
| 8 | | | | 72 |
| 9 | | 43 | | |
| 10 | | 94 | | 50 |
| 13 | | 87 | | |
| 14 | | 91 | | |
| 16 | 100 | | | |
| 17 | | 82 | | |
| 19 | 100 | | | |
| 21 | | 100 | 96 | 65 |
| 22 | | | 100 | 41 |
| 23 | | | | 43 |
| 24 | | 100 | | |
| 28 | | 83 | | 42 |
| 29 | | | | 73 |
| 31 | | 82 | | 50 |
| 33 | | 100 | | 82 |
| 35 | | | 79 | |
| 37 | | | | 70 |
| 44 | | | | 77 |
| 47 | | | | 75 |
| 48 | | | | 57 |
| 50 | 100 | | | |
| 51 | | | | 87 |
| 56 | | 88 | | |
| 57 | | 100 | | |
| 58 | | | | 80 |
| 59 | | | | 80 |
| 61 | | | | 71 |
| 63 | | | | 41 |
| 65 | 100 | | | |
| 66 | | | | 46 |
| 68 | | | | 36 |
| 69 | | | | 78 |

TABLE 3-continued

| Compound No. | Dose (mg/kg) 100 | 50 | 25 | 12.5 |
|---|---|---|---|---|
| 70 | | | | 72 |
| 71 | | | | 74 |
| 72 | | | | 78 |
| 73 | | | | 76 |
| 75 | | | | 57 |
| 76 | | | | 53 |
| 77 | | | | 84 |
| 78 | | | | 82 |
| 79 | | | | 46 |
| 80 | | | | 78 |
| 81 | | | | 57 |
| 82 | | | | 53 |
| 83 | | | | 52 |
| 84 | | | | 69 |
| 85 | | | | 87 |
| 86 | | | | 43 |
| 87 | | | | 78 |
| 88 | | | | 40 |
| 89 | | | | 77 |
| 90 | | | | 94 |
| 91 | | | | 86 |
| 92 | | | | 43 |
| 93 | | | | 82 |
| 95 | | | | 56 |
| 101 | | | | 51 |
| 102 | | | | 42 |
| 103 | | | | 65 |
| 104 | | | | 42 |
| 105 | | | | 92 |
| 106 | | | | 86 |
| 107 | | | | 74 |
| 108 | | | | 94 |

Note:
The numerical value indicates the inhibition rate (%).

TEST EXAMPLE 2

Acute Toxicity

Using DDY male mice of five weeks old, each group consisted of five mice. A test compound was suspended in saline containing 0.5% by weight of CMC and intraperitonially injected at a dose of 0.1 ml/10 g. 24 hours after the injection, survival or death was observed, and the number of death/the number of tested animals was obtained, and the 50% lethal dose $LD_{50}$ was estimated, whereby $LD_{50}$ of each of Compound Nos. 4, 9, 10, 15, 21, 25, 30, 33, 37, 44, 47, 58, 60 and 67 was at least 100 mg/kg.

TEST EXAMPLE 3

A drug having a test compound suspended in saline containing 0.5% by weight of CMC, was intraperitonially administered to SD male rats of seven weeks old so that the dose would be 50 mg/kg. 30 minutes after the injection of the drug, lipopolysaccharide derived from *E. coli* (manufactured by Difco Company, Product No. 0127:B8) was intravenously injected into the tail vein of each rat so that the dose would be 10 mg/kg. Three hours after the injection of the lipopolysaccharide, the drug was again intraperitonially administered in the same amount.

48 hours after the injection of the lipopolysaccharide, survival or death of the rat was observed, and the survival rate was obtained by the following formula, whereby with Compound No. 71, the survival rate was 100%, with Compound No. 73, the survival rate was 75%, and with Compound No. 70, the survival rate was 50.

Further, for the control, the test was conducted in the same manner except that no test compound was added, whereby with the control corresponding to the test group for each of Compound Nos. 70, 71 and 73, the survival rate was 0%.

Survival rate (%)=(number of survived animals/number of tested animals)×100

TEST EXAMPLE 4

A drug having a test compound dissolved in the form of its $Na^+$ salt or or $Cl^-$ salt in saline or suspended in saline containing 0.5% by weight of CMC, was intraperitonially injected to DDY male mice of five weeks old so that the dose would be 100 mg/kg. One hour after the injection of the drug, a solution (containing 1% by weight of dimethylsulfoxide) having a platelet-activating factor (PAF) dissolved in saline to a concentration of 10 µg/ml, was intravenously injected into the tail vein of each mouse in an amount of 15 ml/kg.

One hour after the injection of PAF, survival or death of each mouse was observed, and the survival rate was obtained by the following formula, whereby with Compound Nos. 21, 47, 71 and 78, the survival rate was 100%, and with Compound No. 22, the survival rate was 80%.

Further, for the control, the test was conducted in the same manner except that no test compound was added, whereby with each control corresponding to the test group for each of Compound Nos. 21, 71 and 78, the survival rate was 0%, and in the case of Compound Nos. 22 and 47, the survival rate of the control was 14%.

Survival rate (%)=(number of survived animals/number of tested animals)×100

TEST EXAMPLE 5

A drug having a test compound dissolved in the form of its $Na^+$ salt or or $Cl^-$ salt in saline or suspended in saline containing 0.5% by weight of CMC, was intraperitonially injected to SD male rats of seven weeks old so that the dose of the test compound would be 12.5 mg/kg. 30 minutes after the injection of the drug, a solution (containing 1% by weight of dimethylsulfoxide) having PAF dissolved in saline to a concentration of 10 µg/ml, was intravenously injected into the tail vein of each rat in an amount of 1 ml/kg.

One hour after the injection of PAF, enteric hemorrhage of each rat was inspected, and the degree of hemorrhage was evaluated by the following ratings:

0: No hemorrhage
1: Slight hemorrhage
2: Slight subepithelial congestion
4: Subepithelial congestion over a wide range and slight submucous congestion
6: Submucous congestion over a wide range, flow out of blood from the submucous tissues and necrosis Further, for the control, the test was conducted in the same manner except that no test compound was added, and the inhibition rate was obtained by the following formula, whereby with each of Compound Nos. 69, 71 and 84, the inhibition rate was 100%, with Compound No. 73, the inhibition rate was 92%, and with Compound No. 72, the inhibition rate was 69%.

Inhibition rate (%)=(A−B)/A×100 where

A: rating of the control
B: rating of a rat administered with a test compound

According to the present invention, it is possible to present pyridazinone derivatives of the formula (I) or pharmaceutically acceptable salts thereof, which are useful as anti-shock agents, processes for their production and intermediates for their production.

We claim:

1. A pyridazinone derivative of the formula (I) or a pharmaceutically acceptble salt thereof:

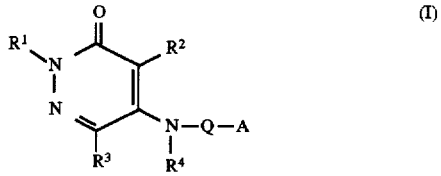

wherein Q is —$CH_2$— or —CO—, A is a furanyl group which may be substituted, a thienyl group which may be substituted, a pyridyl group which may be substituted, a pyridyl N-oxide group which may be substituted, a thiazolyl group which may be substituted, or a phenyl group which may be substituted, $R^1$ is a hydrogen atom, a $C_{1-8}$ alkyl group which may be substituted, a $C_{2-8}$ alkenyl group which may be substituted, a $C_{2-8}$ alkynyl group which may be substituted, or a phenyl group which may be substituted, $R^2$ is a hydrogen atom, a cyano group, a $C_{1-8}$ alkyl group which may be substituted, a hydroxyl group, a $C_{1-8}$ alkoxy group, a dioxanyl group which may be substituted by $C_{1-3}$ alkyl, —CH=N—$R^5$, —S(O)$_n R^6$, —N($R^7$)$R^8$, or —COR$^9$, $R^3$ is a hydrogen atom, a cyano group, $C_{1-8}$ alkoxy group, a carboxyl group or a $C_{1-8}$ alkoxycarbonyl group, $R^4$ is a hydrogen atom, or a $C_{1-8}$ alkyl group which may be substituted, $R^5$ is a $C_{1-8}$ alkoxy group, or a pyridylmethyl group, $R^6$ is a $C_{1-8}$ alkyl group which may be substituted by $C_{1-3}$ alkoxycarbonyl, or a $C_{2-8}$ alkenyl group, each of $R^7$ and $R^8$ independently is a hydrogen atom, a $C_{1-8}$ alkyl group, a $C_{1-8}$ alkylsulfonyl group, a phenylsulfonyl group which may be substituted, a formyl group, a $C_{1-8}$ alkylcarbonyl group which may be substituted by halogen, a $C_{3-8}$ cycloalkylcarbonyl group, or a benzoyl group which may be substituted, $R^9$ is a hydrogen atom, a $C_{1-8}$ alkoxy group, a hydroxyl group, or an amino group which may be substituted by $C_{1-3}$ alkyl or $C_{1-3}$ alkylcarbonyl, n is 0, 1 or 2, provided that when $R^2$ is a hydrogen atom, an alkyl group or an alkoxy group, and Q is —$CH_2$—, A is a furanyl group which may be substituted, a thienyl group which may be substituted, a pyridyl group which may be substituted, a pyridyl N-oxide group which may be substituted, or a thiazolyl group which may be substituted wherein the substituent for each of the furanyl group which may be substituted, the thienyl group which may be substituted, the pyridyl group which may be substituted, the pyridyl N-oxide group which may be substituted and the thiazolyl group which may be substituted, as defined by A, the phenyl group which may be substituted, as defined by A or $R^1$, or the phenylsulfonyl group which may be substituted and the benzoyl group which may be substituted, as defined by $R^7$ or $R^8$, is halogen, nitro, trifluoromethyl, $C_{1-3}$ alkyl, $C_{1-3}$ alkoxy, amino or mono- or di-$C_{1-3}$ alkylamino, the substituent for each of the alkyl group which may be substituted, the alkenyl group which may be substituted and the alkynyl group which may be substituted, as defined by $R^1$, or the alkyl group which may be substituted, as defined by $R^2$ or $R^4$, is halogen, hydroxyl, $C_{1-3}$ alkoxy, $C_{1-3}$ alkylthio, $C_{1-3}$ alkylcarbonyloxy, $C_{1-3}$ alkoxycarbonyloxy, phenyl, amino, mono- or di-$C_{1-3}$ alkylamino, $C_{1-3}$ alkylsulfonylamino, cyano, carboxyl or $C_{1-3}$ alkoxycarbonyl, and wherein when Q is —$CH_2$—, $R^2$ is not hydrogen or alkyl when either (1) $R^1$ is not phenyl or not substituted phenyl or (2) $R^3$ is not cyano, carboxyl or alkoxycarbonyl.

2. The pyridazinone derivative or a pharmaceutically acceptable salt thereof according to claim 1, wherein in the formula (I), Q is —$CH_2$—.

3. The pyridazinone derivative or a pharmaceutically acceptable salt thereof according to claim 1, wherein in the formula (I), A is a pyridyl group which may be substituted.

4. The pyridazinone derivative or a pharmaceutically acceptable salt thereof according to claim 1, wherein in the formula (I), $R^1$ is an alkyl group.

5. The pyridazinone derivative or a pharmaceutically acceptable salt thereof according to claim 1, wherein in the formula (I), $R^3$ is a hydrogen atom.

6. The pyridazinone derivative or a pharmaceutically acceptable salt thereof according to claim 1, wherein in the formula (I), Q is —$CH_2$—, and A is a pyridyl group which may be substituted.

7. The pyridazinone derivative or a pharmaceutically acceptable salt thereof according to claim 6, wherein in the formula (I), $R^1$ is an alkyl group, $R^2$ is an alkyl group which may be substituted by a group selected from the group consisting of halogen, hydroxyl, $C_{1-3}$ alkoxy, $C_{1-3}$ alkylthio, $C_{1-3}$ alkylcarbonyloxy, $C_{1-3}$ alkoxycarbonyloxy, phenyl, amino, mono- or di-$C_{1-3}$ alkylamino, $C_{1-3}$ alkylsulfonylamino, cyano, carboxyl and $C_{1-3}$ alkoxycarbonyl, a cyano group, or —N($R^7$)$R^8$, and each of $R^7$ and $R^8$ independently is a hydrogen atom, an alkyl group, an alkylsulfonyl group, a phenylsulfonyl group which may be substituted, a formyl group, an alkylcarbonyl group which may be substituted by a halogen atom, a cycloalkylcarbonyl group, or a benzoyl group which may be substituted.

8. The pyridazinone derivative or a pharmaceutically acceptable salt thereof according to claim 7, wherein the compound of the formula (I) is 4-hydroxymethyl-2-methyl-5-(4-pyridylmethylamino)pyridazin-3-(2H)-one, 2-tert-butyl-4-hydroxymethyl-5-(4-pyridylmethylamino) pyridazin-3-(2H)-one, 4-methoxymethyl-2-methyl-5-(N-methyl-3-pyridylmethylamino)pyridazin-3-(2H)-one, 4-methoxymethyl-2-methyl-5-(N-methyl-4-pyridylmethylamino)pyridazin-3-(2H)-one, or 4-methoxymethyl-2-methyl-5-(4-pyridylmethylamino) pyridazin-3-(2H)-one.

9. An anti-shock composition comprising a pyridazinone derivative according to claim 1 and a pharmaceutically acceptable carrier.

10. A process for producing a pyridazinone derivative of the formula (I-1) or a pharmaceutically acceptable salt thereof:

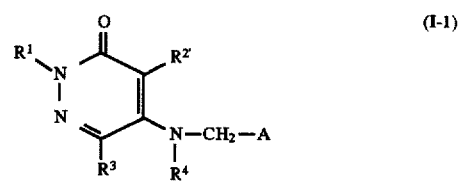

wherein A is a furanyl group which may be substituted, a thienyl group which may be substituted, a pyridyl group which may be substituted, a pyridyl N-oxide group which may be substituted, or a thiazolyl group which may be substituted, or a phenyl group which may be substituted, $R^1$ is a hydrogen atom, a $C_{1-8}$ alkyl group which may be substituted, a $C_{2-8}$ alkenyl group which may be substituted, a $C_{2-8}$ alkynyl group which may be substituted, or a phenyl group which may be substituted, $R^{2'}$ is a hydrogen atom, a cyano group, a $C_{1-8}$ alkyl group which may be substituted, a dioxanyl group which may be substituted by a $C_{1-3}$ alkyl group, —CH=N—R$^5$, or —COR$^9$. R$^3$ is a hydrogen atom, a cyano group, a C$_{1-8}$ alkoxy group, a carboxyl group, or a C$_{1-8}$ alkoxycarbonyl group, R$^4$ is a hydrogen atom, or a C$_{1-8}$ alkyl group which may be substituted, R$^5$ is a C$_{1-8}$ alkoxy group, or a pyridylmethyl group, R$^9$ is a hydrogen atom, a C$_{1-8}$ alkoxy group, a hydroxyl group, or an amino group which may be substituted by C$_{1-3}$ alkyl or C$_{1-3}$ alkylcarbonyl, provided that when R$^{2'}$ is a hydrogen atom or an alkyl group, A is a furanyl group which may be substituted, a thienyl group which may be substituted, a pyridyl group which may be substituted, a pyridyl N-oxide group which may be substituted, or a thiazolyl group which may be substituted, wherein the substituent for each of the furanyl group which may be substituted, the thienyl group which may be substituted, the pyridyl group which may be substituted, the pyridyl N-oxide group which may be substituted and the thiazolyl group which may be substituted, as defined by A, or the phenyl group which may be substituted, as defined by A or R$^1$, is halogen, nitro, trifluoromethyl, C$_{1-3}$ alkyl, C$_{1-3}$ alkoxy, amino or mono- or di-C$_{1-3}$ alkylamino, the substituent for each of the alkyl group which may be substituted, the alkenyl group which may be substituted and the alkynyl group which may be substituted, as defined by R$^1$, or the alkyl group which may be substituted, as defined by R$^{2'}$ or R$^4$, is halogen, hydroxyl, C$_{1-3}$ alkoxy, C$_{1-3}$ alkylthio, C$_{1-3}$ alkylcarbonyloxy, C$_{1-3}$ alkoxycarbonyloxy, phenyl, amino, mono- or di-C$_{1-3}$ alkylamino, C$_{1-3}$ alkylsulfonylamino, cyano, carboxyl or C$_{1-3}$ alkoxycarbonyl, and wherein R$^{2'}$ is not hydrogen or alkyl when either (1) R$^1$ is not phenyl or not substituted phenyl or (2) R$^3$ is not cyano, carboxyl or alkoxycarbonyl which comprises reacting a compound of the formula (II-1):

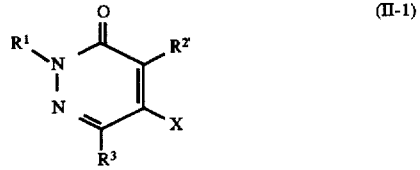

wherein X is a halogen atom or a cyano group, and R$^1$, R$^{2'}$ and R$^3$ are as defined above, with a compound of the formula (III-1):

wherein A and R$^4$ are as defined above.

11. A process for producing a pyridazinone derivative of the formula (I-3) or a pharmaceutically acceptable salt thereof:

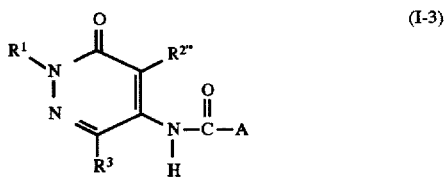

wherein A is a furanyl group which may be substituted, a thienyl group which may be substituted, a pyridyl group which may be substituted, a pyridyl N-oxide group which may be substituted, a thiazolyl group which may be substituted, or a phenyl group which may be substituted, R$^1$ is a hydrogen atom, a C$_{1-8}$ alkyl group which may be substituted, a C$_{2-8}$ alkenyl group which may be substituted, a C$_{2-8}$ alkynyl group which may be substituted, or a phenyl group which may be substituted, R$^{2'''}$ is a hydrogen atom, a cyano group, a C$_{1-8}$ alkyl group which may be substituted, a hydroxyl group, a C$_{1-8}$ alkoxy group, —S(O)$_n$R$^6$, or —N(R$^7$) R$^8$. R$^3$ is a hydrogen atom, a cyano group, a C$_{1-8}$ alkoxy group, a carboxyl group, or a C$_{1-8}$ alkoxycarbonyl group, R$^6$ is a C$_{1-8}$ alkyl group which may be substituted by C$_{1-8}$ alkoxycarbonyl, or a C$_{2-8}$ alkenyl group, each of R$^7$ and R$^8$ independently is a hydrogen atom, a C$_{1-8}$ alkyl group, a C$_{1-8}$ alkysulfonyl group, a phenysulfonyl group which may be substituted, a formyl group, a C$_{1-8}$ alkylcarbonyl group which may be substituted by halogen, a C$_{3-8}$ cycloalkylcarbonyl group, or a benzoyl group which may be substituted, n is 0, 1 or 2, wherein the substituent for each of the furanyl group which may be substituted, the thienyl group which may be substituted, the pyridyl group which may be substituted, the pyridyl N-oxide group which may be substituted and the thiazolyl group which may be substituted, as defined by A, the phenyl group which may be substituted, as defined by A or R$^1$, or the phenylsulfonyl group which may be substituted and the benzoyl group which may be substituted, as defined by R$^7$ or R$^8$, is halogen, nitro, trifluoromethyl, C$_{1-3}$ alkyl, C$_{1-3}$ alkoxy, amino or mono- or di-C$_{1-3}$ alkylamino, the substituent for each of the alkyl group which may be substituted, the alkenyl group which may be substituted and the alkynyl group which may be substituted, as defined by R$^1$, or the alkyl group which may be substituted, as defined by R$^{2'''}$, is halogen, hydroxyl, C$_{1-3}$ alkoxy, C$_{1-3}$ alkylthio, C$_{1-3}$ alkylcarbonyloxy, C$_{1-3}$ alkoxycarbonyloxy, phenyl, amino, mono- or di-C$_{1-3}$ alkylamino, C$_{1-3}$ alkylsulfonylamino, cyano, carboxyl or C$_{1-3}$ alkoxycarbonyl, which comprises reacting a compound of the formula (II-3):

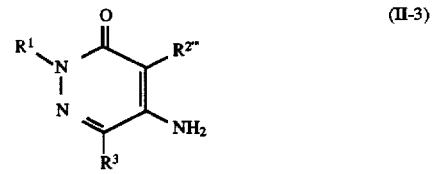

wherein R$^1$, R$^{2'''}$ and R$^3$ are as defined above, with a compound of the formula (III-3) or a reactive derivative thereof:

wherein A is as defined above.

12. A pyridazinone derivative of the formula (II-4) or a salt thereof:

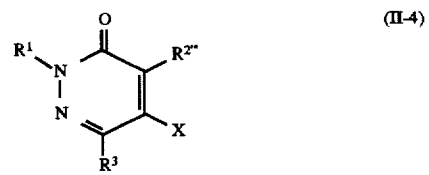

wherein R$^1$ is a hydrogen atom, a C$_{1-8}$ alkyl group which may be substituted, a C$_{2-8}$ alkenyl group which may be substituted, a C$_{2-8}$ alkynyl group which may be substituted, or a phenyl group which may be substituted, R$^3$ is a hydrogen atom, a cyano group, C$_{1-8}$ alkoxy group, a carboxyl group or a C$_{1-8}$ alkoxycarbonyl group, R$^{2''''}$ is a cyano group, a C$_{1-8}$ alkyl group substituted by one or more members selected from the group consisting of halogen, hydroxyl, C$_{1-3}$ alkoxy, C$_{1-3}$ alkylthio, C$_{1-3}$ alkylcarbonyloxy, C$_{1-3}$ alkoxycarbonyloxy, phenyl, amino, mono- or di-C$_{1-3}$ alkylamino, C$_{1-3}$ alkylsulfonylamino and cyano, a dioxanyl group which may be substituted by $C_{1-3}$ alkyl, —CH=N—$R^5$, or —COR$^9$, $R^5$ is a $C_{1-8}$ alkoxy group, or a pyridylmethyl group, $R^9$ is a hydrogen atom, a $C_{1-8}$ alkoxy group, a hydroxyl group, or an amino group which may be substituted by $C_{1-3}$ alkyl or $C_{1-3}$ alkoxycarbonyl, and X is a halogen atom, or a cyano group, wherein the substituent for each of the alkyl group which may be substituted, the alkenyl group which may be substituted, and the alkynyl group which may be substituted, as defined by $R^1$, is halogen, hydroxyl, $C_{1-3}$ alkoxy, $C_{1-3}$ alkylthio, $C_{1-3}$ alkylcarbonyloxy, $C_{1-3}$ alkoxycarbonyloxy, phenyl, amino, mono- or di-$C_{1-3}$ alkylamino, $C_{1-3}$ alkylsulfonylamino, cyano, carboxyl or $C_{1-3}$ alkoxycarbonyl, and the substituent for the phenyl group which may be substituted as defined by $R^1$, is halogen, nitro, trifluoromethyl, $C_{1-3}$ alkyl, $C_{1-3}$ alkoxy, amino or mono- or di-$C_{1-3}$ alkylamino.

* * * * *